(12) United States Patent
Peebles (10) Patent No.: US 8,621,664 B2
(45) Date of Patent: Jan. 7, 2014

(54) COMBINATION HEADGEAR AND EYE PROTECTION SYSTEM

(76) Inventor: Donald Scott Peebles, Bradenton, FL (US)

( * ) Notice: Subject to any disclaimer, the term of this patent is extended or adjusted under 35 U.S.C. 154(b) by 316 days.

(21) Appl. No.: 13/217,035

(22) Filed: Aug. 24, 2011

(65) Prior Publication Data

US 2013/0047310 A1    Feb. 28, 2013

(51) Int. Cl.
    *A41D 13/05*    (2006.01)
(52) U.S. Cl.
    USPC ............................................ 2/15; 2/10; 2/209
(58) Field of Classification Search
    USPC ........... 2/417, 419, 422, 423, 15, 10, 12, 209,
                   2/6.3, 6.5, 6.7, 420, 424, 452, 448;
                   351/158, 118, 119, 121, 123, 140
    See application file for complete search history.

(56) References Cited

U.S. PATENT DOCUMENTS

| 4,856,089 | A |   | 8/1989 | Horton |
|---|---|---|---|---|
| 5,133,596 | A |   | 7/1992 | Korny et al. |
| 5,278,999 | A |   | 1/1994 | Brown et al. |
| 5,373,583 | A | * | 12/1994 | Birum ................................ 2/10 |
| 5,724,119 | A |   | 3/1998 | Leight |
| D404,174 | S |   | 1/1999 | Childs et al. |
| 6,318,369 | B1 |   | 11/2001 | Gregory |
| 6,382,213 | B1 |   | 5/2002 | Sanpei |
| 6,481,846 | B1 |   | 11/2002 | Mikysa |
| 6,511,177 | B1 |   | 1/2003 | Hall et al. |
| 6,611,959 | B1 | * | 9/2003 | Lando ................................. 2/10 |
| 6,892,393 | B1 | * | 5/2005 | Provost et al. ...................... 2/10 |
| 7,020,901 | B2 |   | 4/2006 | Brhel |
| 7,020,903 | B2 |   | 4/2006 | Artzberger |
| 2003/0213051 | A1 | * | 11/2003 | Fournier et al. .................... 2/424 |
| 2005/0015852 | A1 | * | 1/2005 | Brhel ................................. 2/209 |
| 2010/0154093 | A1 | * | 6/2010 | Provost et al. ...................... 2/10 |
| 2010/0175173 | A1 | * | 7/2010 | Sutton ............................... 2/423 |
| 2011/0209273 | A1 | * | 9/2011 | Fountain et al. .................. 2/423 |

FOREIGN PATENT DOCUMENTS

GB          2209923        *   6/1989

* cited by examiner

*Primary Examiner* — Amy Vanatta
(74) *Attorney, Agent, or Firm* — Allen, Dyer, Doppelt, Milbrath & Gilchrist, P.A.

(57) ABSTRACT

A combination headgear assembly and protective eyewear system includes protective eyewear that attaches to a headgear assembly via magnetic connectors. The headgear assembly includes an adjustable headrest with first and second ends. The first end connects to a first spherical capsule having a first side wall, and the second end connects to a second spherical capsule having a second side wall. The protective eyewear includes a vision blade with a first end attaching via a first finger to a first telescoping member while a second end attaches via a second finger to a second telescoping member. A first magnetic connector is positioned between the first telescoping member and the first side wall of the first spherical capsule, and a second magnetic connector is positioned between the first telescoping member and the second side wall of the second spherical capsule.

10 Claims, 8 Drawing Sheets

COMBINATION HEADGEAR AND EYE PROTECTION SYSTEM

FIELD OF THE INVENTION

This invention is directed to a combination headgear and eye protection system. More specifically, the technology relates to a highly adjustable eye protection system that may attach to a headgear assembly via a magnetic ball-and-disc.

BACKGROUND OF THE INVENTION

In certain industrial professions and sporting activities, it is preferable to wear headgear to protect the professional or sportsman's (collectively "user") hearing, due to loud noise. Examples in the professional setting include, but are in no way limited to, construction workers, craftsman, airport ground support, and military personnel. Sportsmen who often encounter loud noises include hunters and any individuals who recreationally use firearms. These individuals must don earplugs, ear muffs or similar headgear in order to prevent hearing loss or injury to the user's ears.

In addition, these users often prefer to use some form of protective eyewear. This is because there is often a risk of eye damage in the event of a misfire of a firearm while engaged in a recreational activity. Likewise, there is always a risk of some form of debris when the user is engaged in a professional activity such as construction, woodworking, or use of heavy machinery.

Numerous limitations exist when a user opts to wear both protective eyewear and headgear. First, it is often cumbersome and uncomfortable to fit eyewear within the headgear to rest and engage the user's ears. Second, it remains difficult for the user to remove and later reposition the eyewear when the user must insert portion of the eyewear within the headgear. Lastly, upon removing the eyewear from inside the headgear and from the user's face, there is often no place to store this protective eyewear for quick and easy retrieval.

There have been only a few forms of combination headgear and protective eyewear assemblies, all of which have considerable limitations. As one example, U.S. Pat. No. 7,020,901 entitled "Eye and Ear Protection Apparatus to Brhel issued on Apr. 5, 2006 discloses an extension member functionally adapted to cooperatively engage and be slideably received within one or more slits found within the eyewear. A flange positioned on the outer surface of the headgear assembly is capable of receiving the slits to engage and hold the eyewear. However, this slit and flange system fails to allow quick attachment and later removal of the eyewear.

As a second example, U.S. Pat. No. 7,020,903 entitled "Combination Ear and Eye Protective Apparatus" teaches a pair of bridge-to-frame hinges that connect between part of bridge portions and the frame ends. Preferably, there are a pair of bridge-to-ear cover connectors that connect to the distal ends of the bridge portions and a pair of ear to cover bridge connectors that connect to the outer portions of the ear covering portions. The bridge-to-ear cover connectors are comprised of first hook-or-loop connectors, and the ear-cover-to-bridge connectors are comprised of second hook-or-loop connectors. Use of such a hook-and-loop assembly fails to create a sufficient bond to secure the headgear to the protective eyewear.

As a third example of a combination assembly, U.S. Pat. No. 6,511,177 entitled "Protective Eyewear with Adjustable Strap," to Hall reference issued on Jan. 28, 2003 teaches use of a "snap lock" which allows the ear muffs or head phones to engage the headband of the protective eyewear. While this provides a more improved fastener compared to a hook and loop fastener, it still provides an awkward assembly should the need arise to quickly remove or attach the protective eyewear if the user has already positioned and is wearing headgear.

Accordingly, there is a need in the art of combination headgear that allows protective eyewear to be quickly and easily secured to headgear, when the headgear is already worn by the user. Moreover, there is a further need for a system that allows the eyewear to be quickly removed and stowed when the user does not need the protective eyewear during a professional or recreational sporting event.

SUMMARY OF THE INVENTION

This invention solves the current limitations in the art of combination headgear assemblies and protective eyewear systems. More specifically, one embodiment of the invention may comprise protective eyewear that attaches to a headgear assembly via magnetic connectors. The headgear assembly may include an adjustable headrest with a first and second end. The first end connects to a first spherical capsule having a first side wall. Similarly, the second end connects to a second spherical capsule having a second side wall.

The protective eyewear may include a vision blade with a first end, a second end, a top end, and a bottom end. The first end attaches via a first finger to a first telescoping member while the second end attaches via a second finger to a second telescoping member. A first magnetic connector is positioned between the first telescoping member and the first side wall of the first spherical capsule. Likewise, a second magnetic connector may be positioned between the first telescoping member and the second side wall of the second spherical capsule. Both spherical capsules may include a comfort pad which allows more comfortable contact on the side of the user's head.

Optionally, the headgear assembly includes both a first and second "U" shaped connector to attach the adjustable headrest to both spherical capsules. The first "U" shaped connector may be attached to the first end of the adjustable headrest having two first sliding members which attach to the first spherical capsule via a first set of pivot pins. Similarly, the second "U" shaped connector may be attached to the second end of the adjustable headrest having two second sliding members which attach to the first spherical capsule via a second set of pivot pins. Each sliding member includes a rotating support which engages a pivot pin on a spherical capsule, where the rotating support in turn engages and is affixed to an outer bar with an internal cavity having a sufficient size and dimension to engage and maintain an inner bar which affixes to the adjustable headrest.

Each telescoping member of the protective eyewear is sufficiently hollow to form a shaft of sufficient size and dimension to position an engaging rod which in turn may engage a side wall of the spherical capsule. The telescoping members both include extensions to provide for greater adjustability of the eyewear. Preferably, both the first and second magnetic connectors are ball-and-disc devices.

BRIEF DESCRIPTION OF THE DRAWINGS

For a fuller understanding of the invention, reference is made to the following detailed description, taken in connection with the accompanying drawings illustrating various embodiments of the present invention, in which.

DETAILED DESCRIPTION OF THE INVENTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 1:
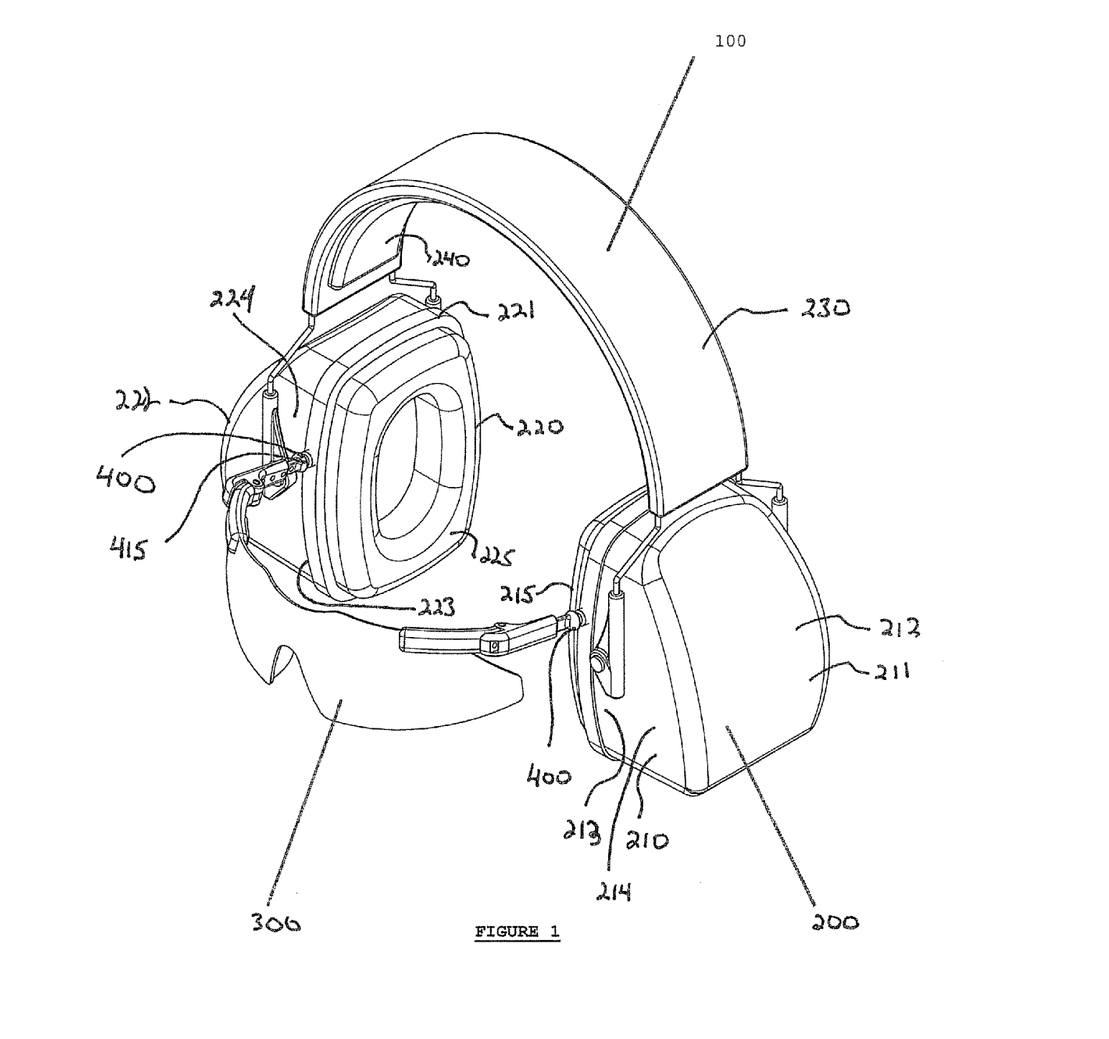
FIG. 1 is a perspective view of the combination headgear and protective eyewear assembly.

FIG. 1 illustrates, by way of example, the overall components of the combination system 100. As shown, there are three primary components of the combination system 100: the headgear assembly 200, the protective eyewear 300, and the magnetic connectors 400 (which connect to both the headgear assembly 200 and the protective eyewear 300). As shown, and disclosed in greater detail below, it is preferable that the magnetic connectors 400 include a ball-and-disc device 415. (The only ball and socket feature is the plastic socket in which the ball magnet is permanently attached. Although utilizing a ball magnet with a mating "socket", or concave, magnet for attachment is feasible, this arrangement does not provide the freedom of movement that the magnetic ball and disc arrangement provides)

Headgear Assembly

Figure 2:
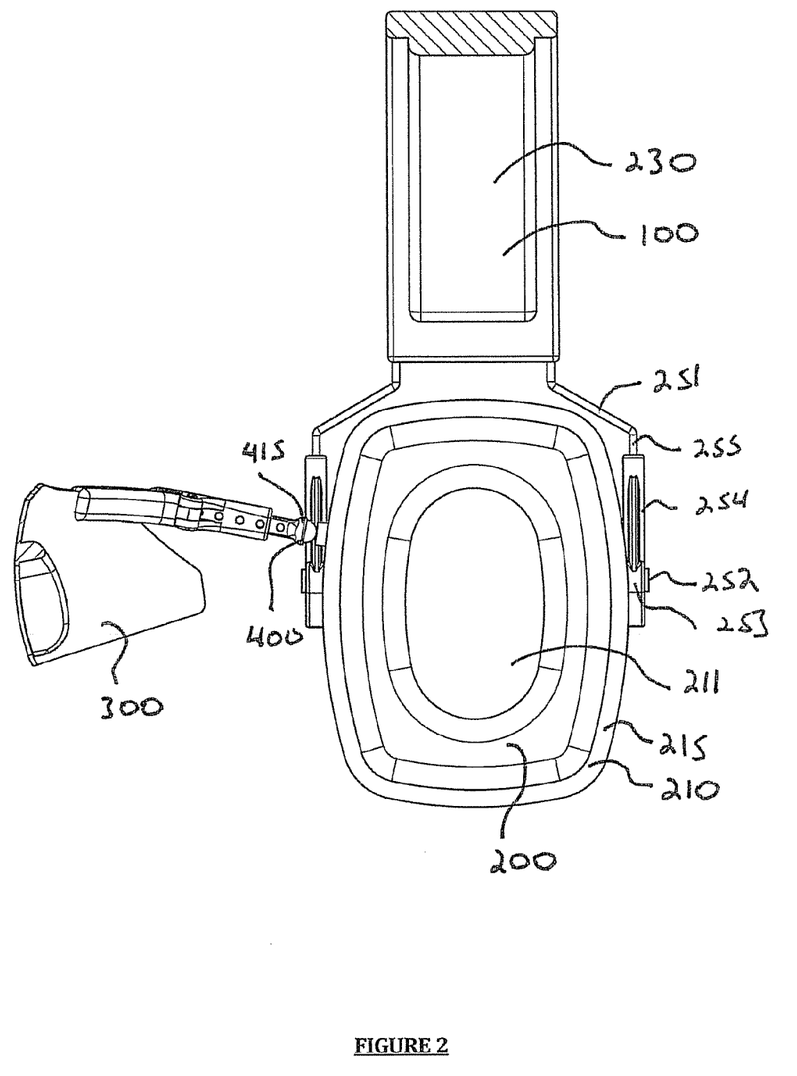
FIG. 2 is a sectioned side view of the combination assembly.

As shown in both FIG. 1 and FIG. 2, the headgear assembly 200 includes three main parts: a first earmuff 210, a second earmuff 220, and an adjustable headrest 230. As shown in FIG. 1, the adjustable headrest 230 connects to both the first earmuff 210 and second earmuff 220. Preferably, the earmuffs 210 and 220 are made out of a lightweight, resilient and sound reducing material such as a plastic, composite, polymer or metal. Moreover, the inner portion of both earmuffs 210 and 220 may be lined with sound reducing materials.

Both earmuffs 210 and 220 are elliptical in cross section having a sufficient diameter and height so as to enclose and cover the user's ears. Moreover, both earmuffs 210 and 220 include spherical capsules 211 and 221 that mirror each other in size and configuration. The first spherical capsule 211 includes a first end 212, a corresponding second end 213, and a side wall 214. Likewise, the second spherical capsule 221 includes a first end 222, corresponding second end 223, and a side wall 224.

As shown in both FIG. 1 and FIG. 2, the second ends 213 and 223 both engage soft and pliant pads 215 and 225. Both soft and pliant pads 215 and 225 function to allow the headgear assembly 200 to comfortably sit about the user's head. While numerous materials are contemplated for the pads 215 and 225, they are preferably made of neoprene or similar sponge like material. However, other similarly lightweight and resilient materials, known to those skilled in the art, may be used.

Figure 3:
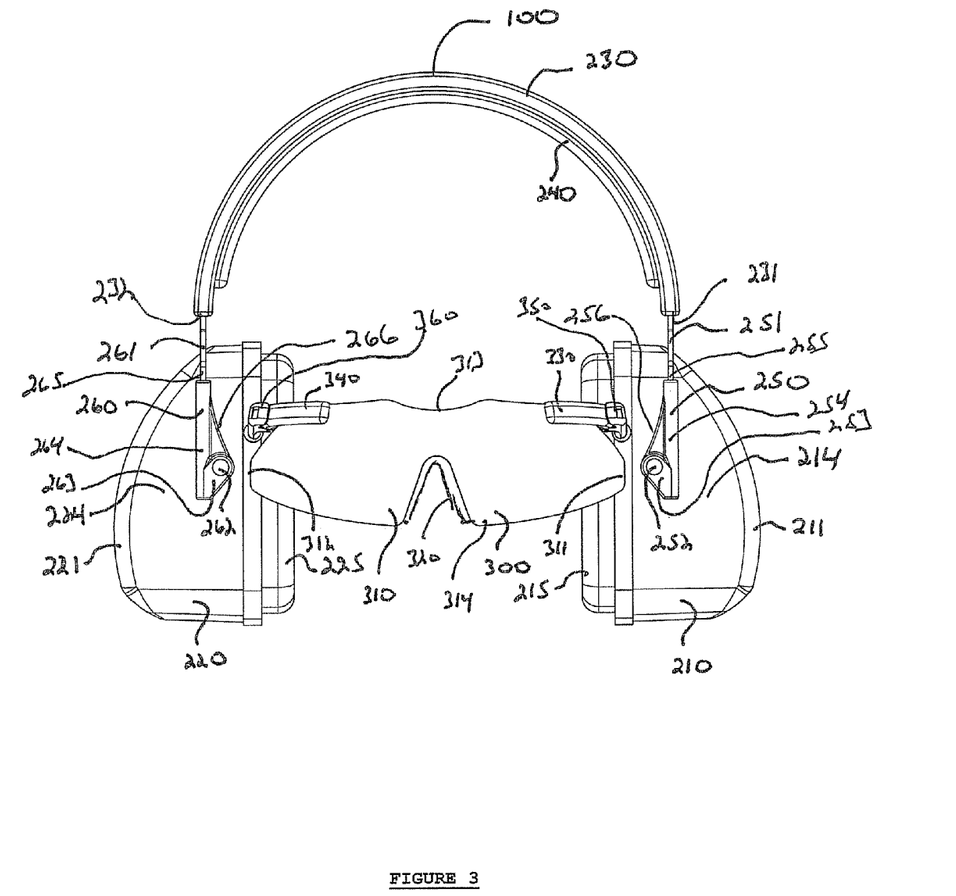
FIG. 3 is a front view of the combination assembly.

FIG. 3 and illustrates, by way of example, the salient components of the adjustable headrest 230. As shown, the adjustable headrest 230 may include a top cushion 240, a first sliding member 250 and a corresponding second sliding member 260. The first sliding member 250 rotateably connects to the side wall 214 of the first spherical capsule 211. Likewise, the second sliding member 260 connects to the side wall 224 of the second spherical capsule 221.

Figure 4:
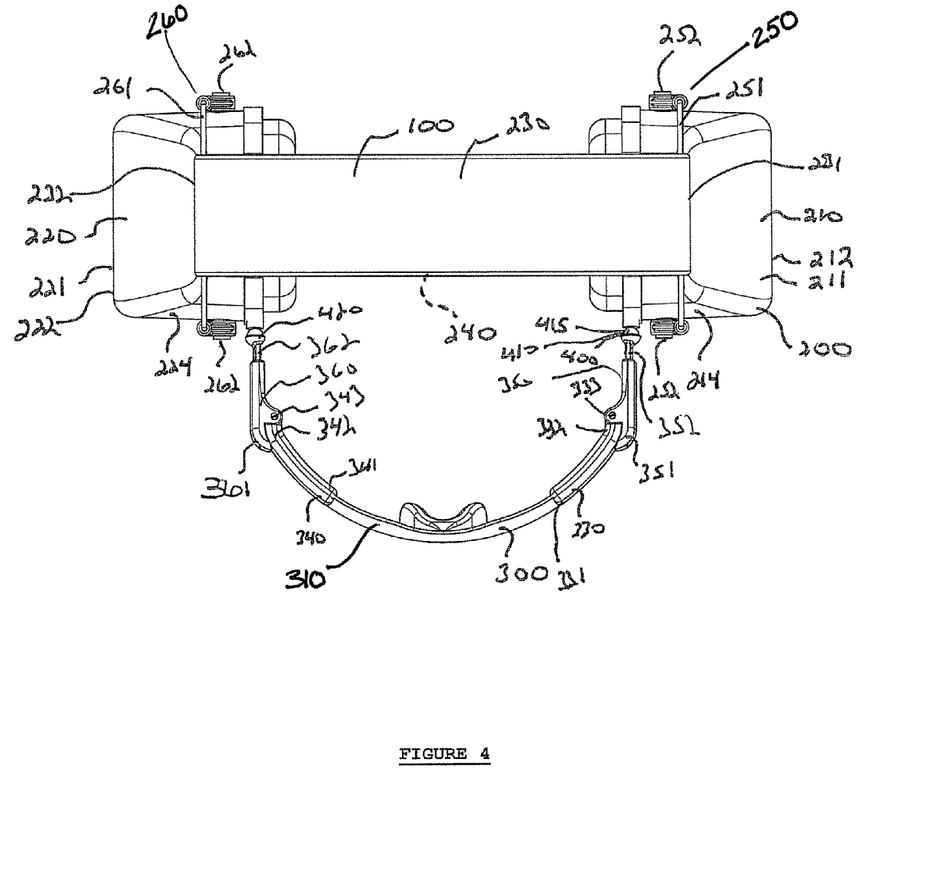
FIG. 4 is a top view of the combination assembly.

As shown in FIG. 4, the first sliding member 250 includes a first "U" shaped connector 251 that engages the first side wall 214 through use of two pivot pins 252. Correspondingly, the second sliding member 260 includes a second "U" shaped connector 261 that engages the first side wall 224 via two pivot pins 262. Both "U" shaped connectors 251 and 261 have a sufficient size and dimension to fit about both spherical capsules 211 and 221. All four pivot pins (252 and 262) connect to the earmuffs 210 and 220 so as to allow a custom fit about the user's head.

As further shown in FIG. 4, the adjustable headrest 230 includes a first end 231 and a corresponding second end 232. The first end 231 engages the first "U" sliding connector 251 through the first connecting member 250. Likewise, the second end 232 connects the second "U" shaped connector 261 through the second sliding member 260.

Both FIG. 2 and FIG. 3 illustrate the arrangement and functionality of both the first and second sliding members 250 and 260 of the headgear assembly 200. As shown and illustrated, there are two first sliding members 250 which engage the first "U" connector 251.

Each first sliding member 250 has three primary components: a rotating support 253, an outer bar 254 and an inner bar 255. As shown and illustrated in FIG. 3, each rotating support 253 is configured to engage a pivot pin 252. This allows the rotating support 253 to move about the first spherical capsule 211. The outer bar 254 is directly attached to the rotating support 253, and may include a stabilizing beam 256. Such outer bar 254 is preferably hollow and capable of receiving and maintaining the inner bar 255. Such inner bar 255 directly attaches to the first end 231 of the adjustable headrest 230.

Likewise, FIG. 3 further shows how the second sliding member 260 parallels construction of the first sliding member 250. More specifically, the second sliding member 260 includes a rotating support 263, an outer bar 264, and an inner bar 265. Such inner bar 265 direct attaches to the second end 231 of the adjustable headrest 230.

Protective Eyewear

Both FIG. 3 and FIG. 4 illustrate, by way of example, the salient components of the protective eyewear 300. FIG. 4 best shows the primary components of the protective eyewear 300. First, the protective eyewear 300 includes a visor blade 310 that is made from a hard and sturdy glass or polymer that acts and functions as a shield. The visor blade 310 includes a first side 311, a corresponding second side 312, a top side 313 and a corresponding bottom side 314. As shown in FIG. 3, the bottom side 314 of the visor blade 310 includes a curved nose pad 320 that allows the protective eyewear 300 to rest upon the user's nose.

As is further shown in FIG. 3, the first side 311 is engaged by a first finger 330 while the second side 312 is affixed to a second finger 340. As illustrated in FIG. 4, both fingers 330 and 340 are slightly curved and have a first end (331 and 341) and a second end (332 and 342). The second end 332 engages a first telescoping member 350 through a pivot pin 333. Of similar construction, the second finger 340 likewise connects to a second telescoping member 360 via a pivot pin 343.

The structure and arrangement of both telescoping members 350 and 360 provided improved functionality and safety features. In addition, the telescoping members 350 and 360 are both sufficiently hollow as to form shafts 353 and 363. As such, a first engaging rod 352 is of a sufficient size and dimension to be positioned within the first shaft 353. Likewise, a second engaging rod 362 is partially enclosed by the second shaft 363. These telescoping members 350 and 360 both include "by-pass" extensions 351 and 361 in order to by-pass the pivot pin connection and provide additional length, forward of the pivot pin connection 333 and 343. This additional length, forward of the pivot pin connection, provides more engagement and travel between the engaging rods 352 and 362 and telescoping members 350 and 360. Due to the size of the earmuff cup covering the ear, there is limited available space between the cup and the pivot pin area of the eyewear. This is especially true of persons with the shortest "ear-to-front-of-face" dimensions. Extending past this pivot pin area allows for longer telescoping members 350 and 360 and more adjustability of engaging rods 352 and 362. Additionally, by extending past this pivot pin area, the rectangular female shaft 353 and 363 is able to completely pass through the telescoping member 350 and 360. This pass-through shaft allows the engaging rods 352 and 362 to be made oversized (longer) so device can be fitted to persons with the longest "ear-to-front-of-face" dimensions. For persons with shorter dimensions, the excess length of the engaging rod 352 and 362 can be trimmed off once the person determines the excess length is not needed. This extension feature 351 and 361 is not found in traditional eyewear due to the fact that traditional eyewear is not designed to be adapted to earmuff type head gear as described in this invention. This feature allows for a longer engaging rod which in turn will provide greater adjustability of the engaging rod, fitting a broader range of users.

Magnetic Connectors

FIGS. 4 through 8 illustrate, by way of example, the components of the magnetic connectors 400. First turning to FIG. 4, a first magnetic connector 410 is affixed to a first engaging rod 352. Likewise, a second magnetic connector 420 is affixed to the second engaging rod 362. In turn, a portion of both magnetic connectors 410 and 420 affixes to the headgear assembly 200.

Figure 5:
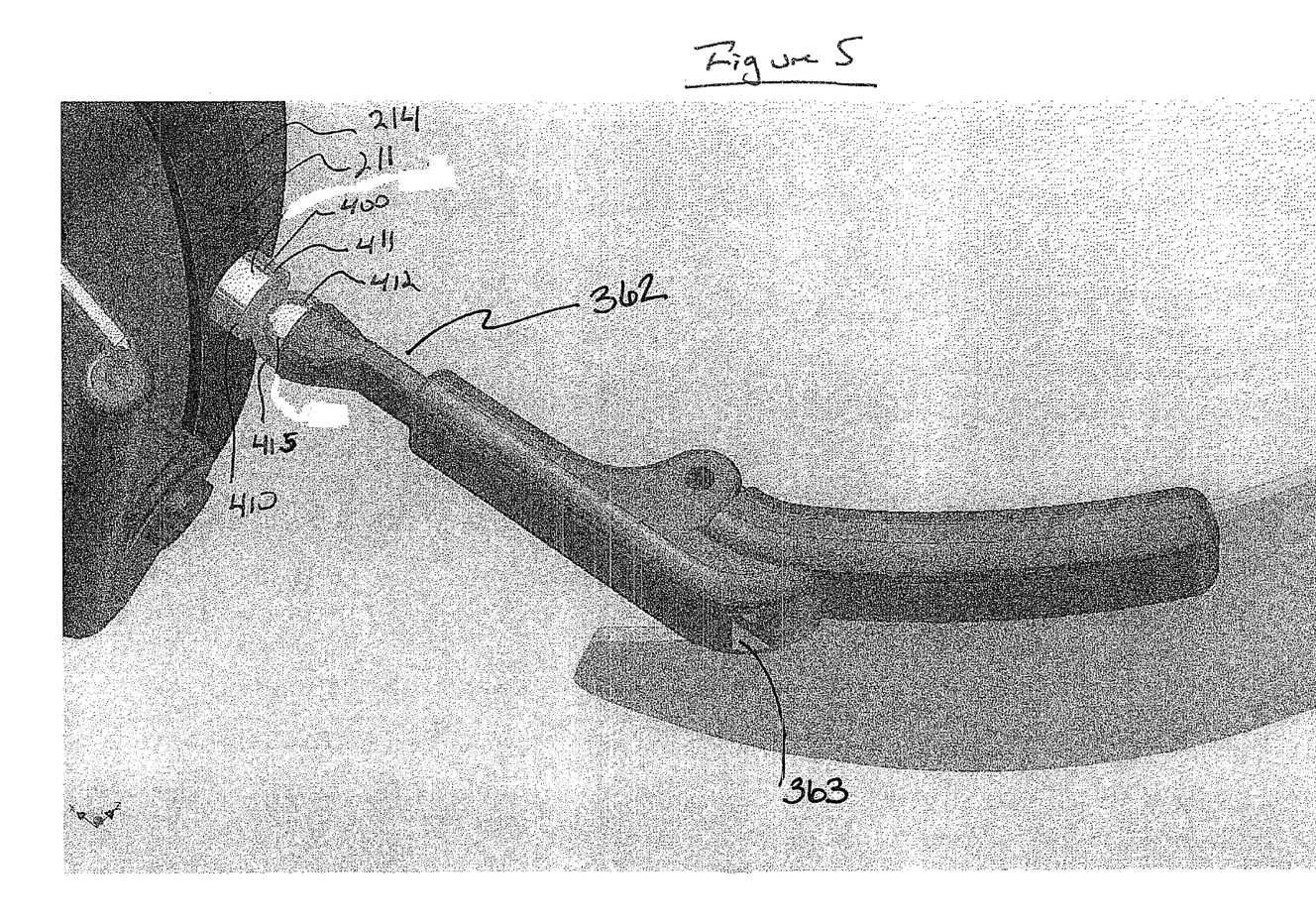
FIG. 5 is a perspective view illustrating the magnetic connector.
Figure 6:
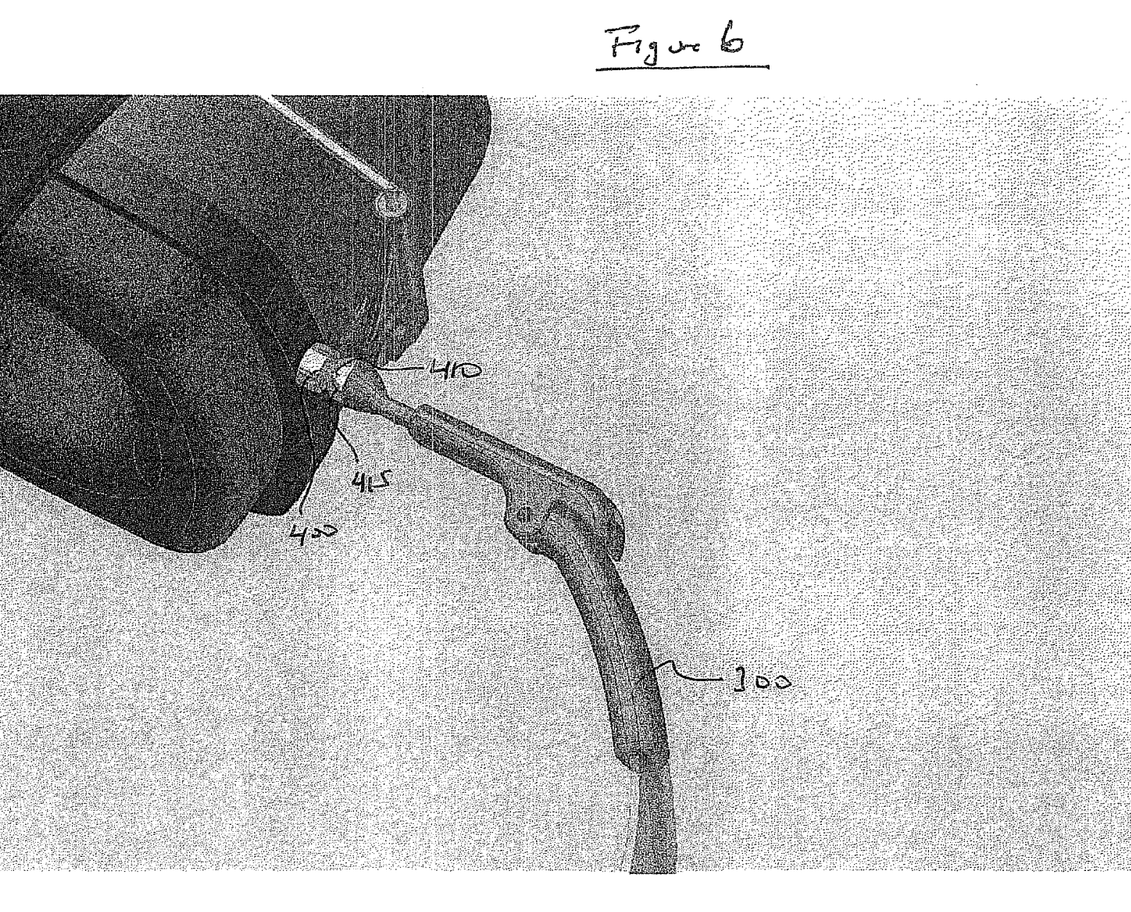
FIG. 6 is a first perspective view illustrating the telescoping member which engages the magnetic connector.
Figure 7:
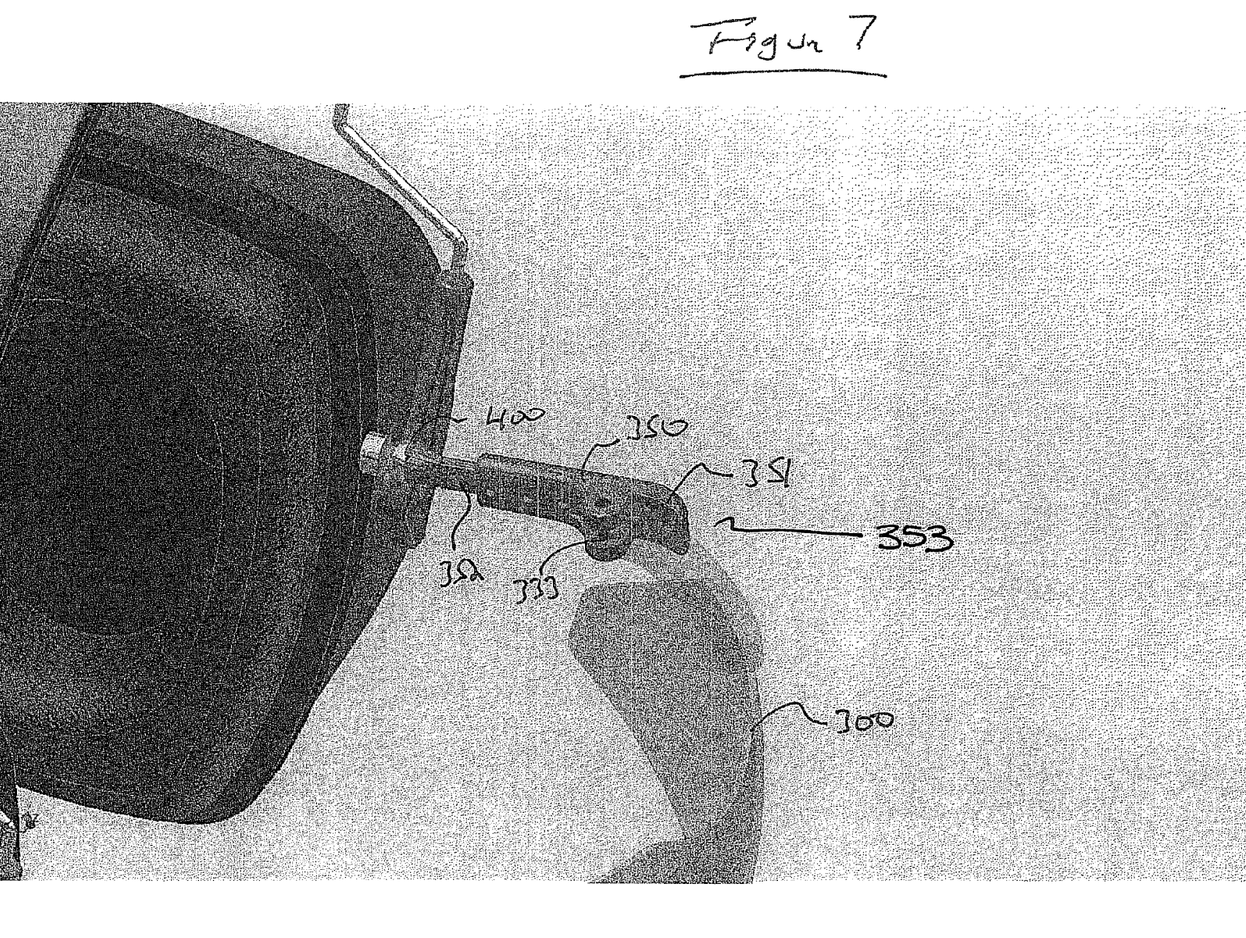
FIG. 7 is a second perspective view showing a ball-and-disc device as the magnetic connector.
Figure 8:
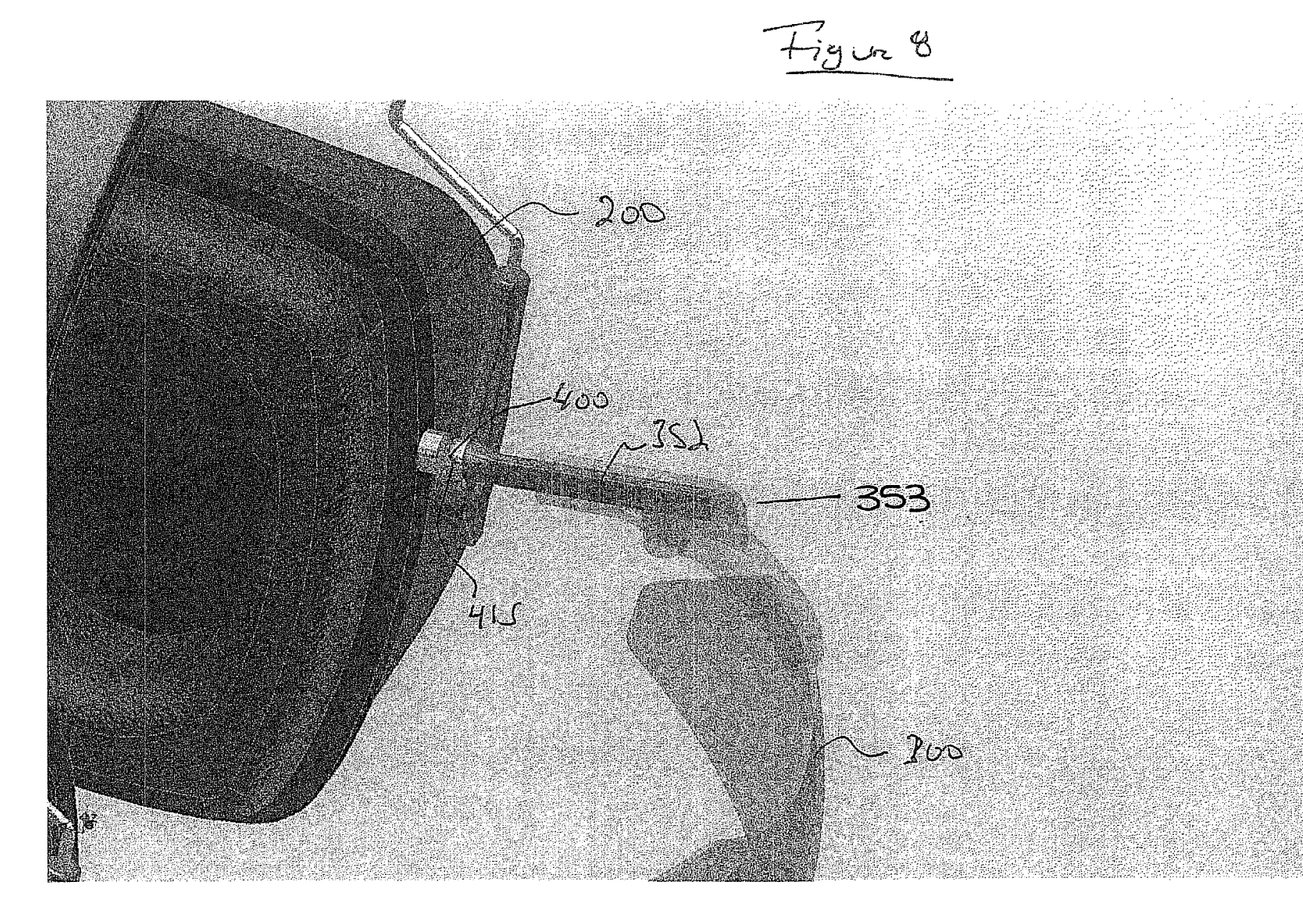
FIG. 8 is a third perspective view showing the magnetic connector attaching to the headgear assembly.

As provided in greater detail in both FIG. 4 and FIG. 5, the first magnetic connector 410 includes both a cylindrical disc magnet 411 and a ball magnet 412. The ball magnet 412 directly attaches to the first engaging rod 352 positioned on the protective eyewear 300.

As further shown in FIG. 4 and FIG. 5, the cylindrical disc magnet 411 magnetically attaches to a ball magnet 412. Under such arrangement, the magnetic connector 410 is arranged as a magnetic ball-and-disc device 415. Here, the disc 411 is permanently affixed to the side wall 214 of the first spherical capsule 211. Similarly, the disc 411 of the second magnetic connector 420 is permanently affixed to the second spherical capsule 221.

Under the assembly shown in FIGS. 4 through 8, the protective eyewear 300 can be easily affixed to the headgear 200 through the magnetic connectors 400. Likewise, the protective eyewear 300 can be quickly removed when not in use via the magnetic connectors 400.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

I claim:

1. A combination headgear assembly and protective eyewear system comprising:
   a headgear assembly having an adjustable headrest with a first end and a second end, the first end connecting to a first capsule having a first side wall and the second end connecting to a second capsule having a second side wall;
   protective eyewear having a vision blade with a first end, a second end, a top end, and a bottom end, wherein the first end attaches via a first finger to a first telescoping member while the second end attaches via a second finger to a second telescoping member;
   a first magnetic connector positioned between the first telescoping member and the first side wall of the first capsule; and
   a second magnetic connector positioned between the second telescoping member and the second side wall of the second capsule.

2. The system of claim 1, wherein the headgear assembly further comprises:
   a first "U" shaped connector attached to the first end of the adjustable headrest having two first sliding members which attach to the first capsule via a first set of pivot pins; and
   a second "U" shaped connector attached to the second end of the adjustable headrest having two second sliding members which attach to the second capsule via a second set of pivot pins.

3. The system of claim 2, wherein each sliding member includes a rotating support which engages a pivot pin on the capsule, where the rotating support in turn engages and is affixed to an outer bar with an internal cavity having a sufficient size and dimension to engage and maintain an inner bar which affixes to the adjustable headrest.

4. The system of claim 1, wherein each telescoping member is sufficiently hollow to form a shaft of sufficient size and dimension to position an engaging rod which in turn may engage a side wall of the capsule.

5. The system of claim 4, wherein the telescoping members both include by-bass extensions to allow for a longer telescoping member as well as a pass-through shaft in the telescoping member.

6. The system of claim 1, wherein the first magnetic connector is a ball-and-disc device.

7. The system of claim 1, wherein the second magnetic connector is a ball-and-disc device.

8. The system of claim 1, wherein the bottom end of the vision blade includes a nose pad.

9. The system of claim 8, wherein the first capsule comprises a spherical shape and includes a comfort pad.

10. The combination system of claim 8, wherein the second capsule comprises a spherical shape and includes a comfort pad.

* * * * *